(12) United States Patent
Fernandez

(10) Patent No.: US 9,268,827 B2
(45) Date of Patent: Feb. 23, 2016

(54) SYSTEM AND METHOD FOR COLLECTING DATA FROM DATA SOURCES AND USING DATA COLLECTION TOOLS

(75) Inventor: Ronald E. Fernandez, Ann arbor, MI (US)

(73) Assignee: Unival, Inc., Ann Arbor, MI (US)

( * ) Notice: Subject to any disclaimer, the term of this patent is extended or adjusted under 35 U.S.C. 154(b) by 460 days.

(21) Appl. No.: 12/231,176

(22) Filed: Aug. 29, 2008

(65) Prior Publication Data

US 2009/0006483 A1   Jan. 1, 2009

Related U.S. Application Data

(60) Division of application No. 11/099,878, filed on Apr. 6, 2005, now abandoned, and a continuation-in-part of application No. 10/989,989, filed on Nov. 16, 2004, now Pat. No. 7,519,622.

(51) Int. Cl.
*G06F 17/30* (2006.01)
*G06F 19/00* (2011.01)

(52) U.S. Cl.
CPC ........ *G06F 17/30557* (2013.01); *G06F 19/322* (2013.01)

(58) Field of Classification Search
CPC .............. G06F 19/322; G06F 19/3418; G06F 12/0866; G06F 12/128; G06F 13/24; G06F 17/30067; G06F 19/325; G06F 19/327; G06F 19/328; G06F 19/3425; G06F 19/345; G06F 19/363; G06F 9/4825; G06F 17/30557
See application file for complete search history.

(56) References Cited

U.S. PATENT DOCUMENTS

| | | | |
|---|---|---|---|
| 5,475,742 A | 12/1995 | Gilbert | |
| 5,745,681 A | 4/1998 | Levine et al. | |
| 5,924,074 A * | 7/1999 | Evans | 705/3 |
| 5,950,010 A * | 9/1999 | Hesse et al. | 717/178 |
| 6,006,230 A | 12/1999 | Ludwig et al. | |
| 6,163,276 A | 12/2000 | Irving et al. | |
| 6,460,041 B2 | 10/2002 | Lloyd | |
| 6,691,116 B1 | 2/2004 | Bart | |
| 6,751,650 B1 | 6/2004 | Finch et al. | |
| 2001/0016822 A1 * | 8/2001 | Bessette | 705/3 |
| 2002/0077849 A1 * | 6/2002 | Baruch et al. | 705/2 |
| 2002/0128866 A1 * | 9/2002 | Goetzke et al. | 705/2 |
| 2002/0194314 A1 | 12/2002 | Kouznetsov et al. | |
| 2003/0014282 A1 * | 1/2003 | Haaksma et al. | 705/3 |
| 2004/0153338 A1 | 8/2004 | Kim et al. | |
| 2006/0106787 A1 | 5/2006 | Fernandez | |

OTHER PUBLICATIONS

Notice of Allowance for U.S. Appl. No. 10/989,989 mailed Dec. 12, 2008.

* cited by examiner

*Primary Examiner* — Dinku Gebresenbet
(74) *Attorney, Agent, or Firm* — Brinks Gilson & Lione

(57) ABSTRACT

A system and a method for collecting data from a data source that includes a database containing a tool for collecting data from the data source and creating a data record, a tool selector in communication with the database for selecting the tool from the database, a tool processor for executing the tool, and a communication channel for communicating between the database and the tool processor. The tool is selected from the database by the tool selector and transmitted via the communication channel to the tool processor for use in creating a data record that is transmitted to the database via the communication channel.

8 Claims, 5 Drawing Sheets

SYSTEM AND METHOD FOR COLLECTING DATA FROM DATA SOURCES AND USING DATA COLLECTION TOOLS

RELATED APPLICATIONS

This application is a divisional application that claims the benefit of U.S. Ser. No. 11/099,878 filed on Apr. 6, 2005, which is a continuation-in-part application that claims the benefit of the utility application entitled "SYSTEM AND METHOD FOR COLLECTING DATA FROM DATA SOURCES USING DATA COLLECTION TOOLS" (Ser. No. 10/989,989) filed on Nov. 16, 2004, both of which are hereby incorporated by reference in their entirely.

TECHNICAL FIELD

This invention relates generally to the field of data collection, and more specifically to a new and useful system and method for collecting data from data sources using data collection tools that function through either an automated interface or a human operator.

BACKGROUND

Specific information relevant to the health of a patient may be stored in files, records, and other data sources located in many different medical facilities such as physician offices, hospitals, skilled nursing facilities, medical laboratories, free standing radiology clinics and other health care providers. Patient information is often required by organizations that are authorized to receive such information, such as medical service provider plans, governmental agencies, including Medicare and Medicaid, and other authorized organizations. The specific information may be found in many locations, on various media, in numerous formats and amid a considerable amount of non-relevant data. For example, data collection may take the form of extracting data from electronic or paper files and records or collecting data visually by inspection during an on-site audit of a medical facility. Selecting, collecting, abstracting, and organizing the relevant data into a format that is readily analyzed by the resources of a medical service provider plan or other authorized organization is a complex and time consuming task. Thus, authorized organizations have a need for new and efficient systems and methods for selecting, collecting, abstracting and organizing specific medical information from the files of their participating medical and healthcare service providers.

SUMMARY

In one aspect of the invention, a system is provided for collecting data from a data source and creating data records that includes a database containing tools for collecting the data from the data sources and creating data records. A tool selector in communication with the database is also provided for selecting a tool from the database, and a tool processor for executing the tool. A communication channel communicates between the database and the tool processor enabling a tool to be selected by a tool selector program running on an application processor and transmitted to the tool processor for use in creating a data record, which is transmitted to the database via the communication channel.

In another aspect of the invention, a method is described in which a tool is selected from a database and transmitted from the database to a tool processor by way of a communication channel for use by either a human operator or by an application interface program to facilitate the collection of data from a data source and the creation of a data record, which is transmitted from the tool processor to the database via the communication channel.

These and other aspects and advantages of the present invention will become apparent upon reading the following detailed description of the invention in combination with the accompanying drawings.

DESCRIPTION OF THE PREFERRED EMBODIMENT

The following description of the preferred embodiment of the invention is not intended to limit the invention to this preferred embodiment, but rather to enable any person skilled in the art of data collection to make and use this invention.

Figure 1:
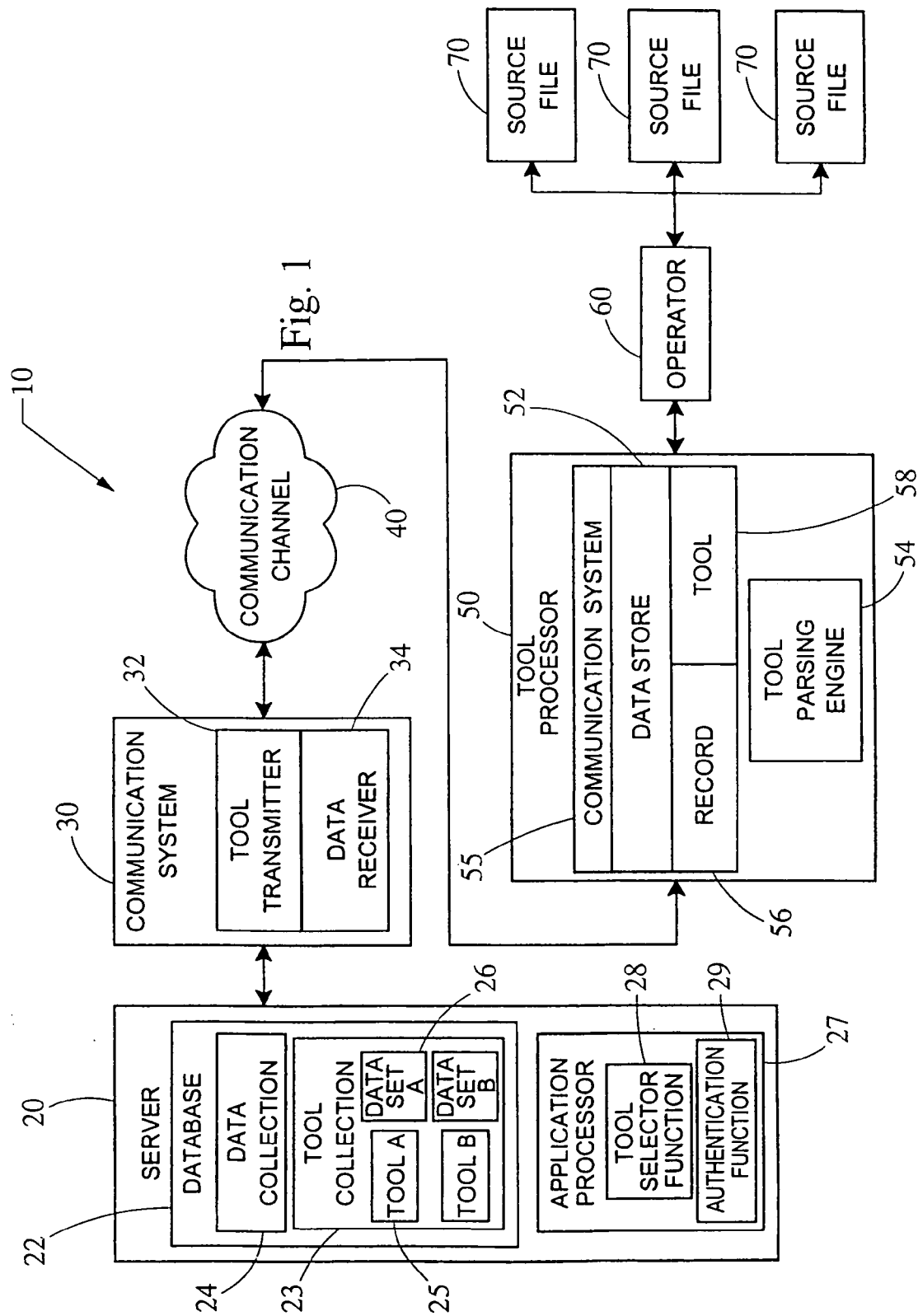
FIG. 1 is a block diagram showing the architecture and functional entities of a first embodiment of the invention having a human operator.

As shown in FIG. 1, the first preferred embodiment of the system 10 for collecting data from a data source includes a server 20 linked to a communication system 30. The server 20 contains a database 22 in communication with an application processor 27. The application processor 27 has a tool selector functionality 28 for selecting tools appropriate for a given data collection assignment and an authentication functionality 29 to identify particular operators 60 who operate or interface with the tool processors 50. The authentication functionality 29 enables the particular data collection assignments that have been assigned to the operators 60 to be correlated with the correct operator 60.

The application processor 27 may be resident on the same physical machine or server 20 as the database 22 or could be physically separated from the database 22 and residing on a separate machine. The database 22 contains a data collection 24 and a tool collection 23. The tool collection 23 contains at least one data tool 25, but could contain a suite of diverse data tools 25 for collecting data, each data tool 25 being linked or associated with a data set 26. Each data set 26 contains parameters and other information and data that are useful in the execution of the associated or linked data tool 25.

The communication system 30 contains a tool transmitter 32 for transmitting the data tools 25 and data sets 26 to the tool processor 50 and a data receiver 34 for receiving data records created by the operator 60 based on information contained in the source files 70. The data records are stored in the data collection 24 residing on the server 20. The communication system 30 allows a remote server 27 to communicate through a communication channel 40 with the tool processor 50. The tool processor 50 includes a data store 52, in which the data records 56 and data tools 58 are stored. Also included within the tool processor 50 is a tool parsing engine 54 for parsing and executing instructions that form the code or script of the data tools 25 and a local communication system 55 for establishing communication between the operator 60 and the application processor 27 through the communication channel 40. The communication channel 40 and the other links between the various components of the system 10 may be dedicated facilities, a Wide Area Network (WAN), a Virtual Private Network (VPN), a local area network, the internet or any number of other land based, terrestrial based or wireless communication facilities, networks or resources.

The tool processor 50 is utilized by an operator 60 that has access to source files 70. The tool processor 50 may be a PDA, workstation, laptop computer, desktop computer or any other of various platforms containing processing units capable of executing the data tool 25 to create data records 56. In the preferred embodiment depicted in FIG. 1, the operator 60 is a human agent who may be assigned to read through source files 70 that are paper and/or electronic files in a physician's office, hospital, skilled nursing facility, medical laboratory, free standing radiology clinic or other health care provider at any other location or facility of an entity that participates in the medical service provider plan. Alternatively, the system 10 may be configured to function in a more automated way by replacing the human operator 60 with an automated interface application 61, as described below in reference to FIGS. 4 and 5.

The specific information or data that the operator 60 is assigned to collect may be found in source files 70 that are of various media and in numerous formats. The sources files 70 from which the operator 60 may extract the information or data may be electronic or paper files and records or the operator may collect the data or information source files 70 that are the physical locations or facilities themselves by inspecting or auditing the premises.

Figure 2:
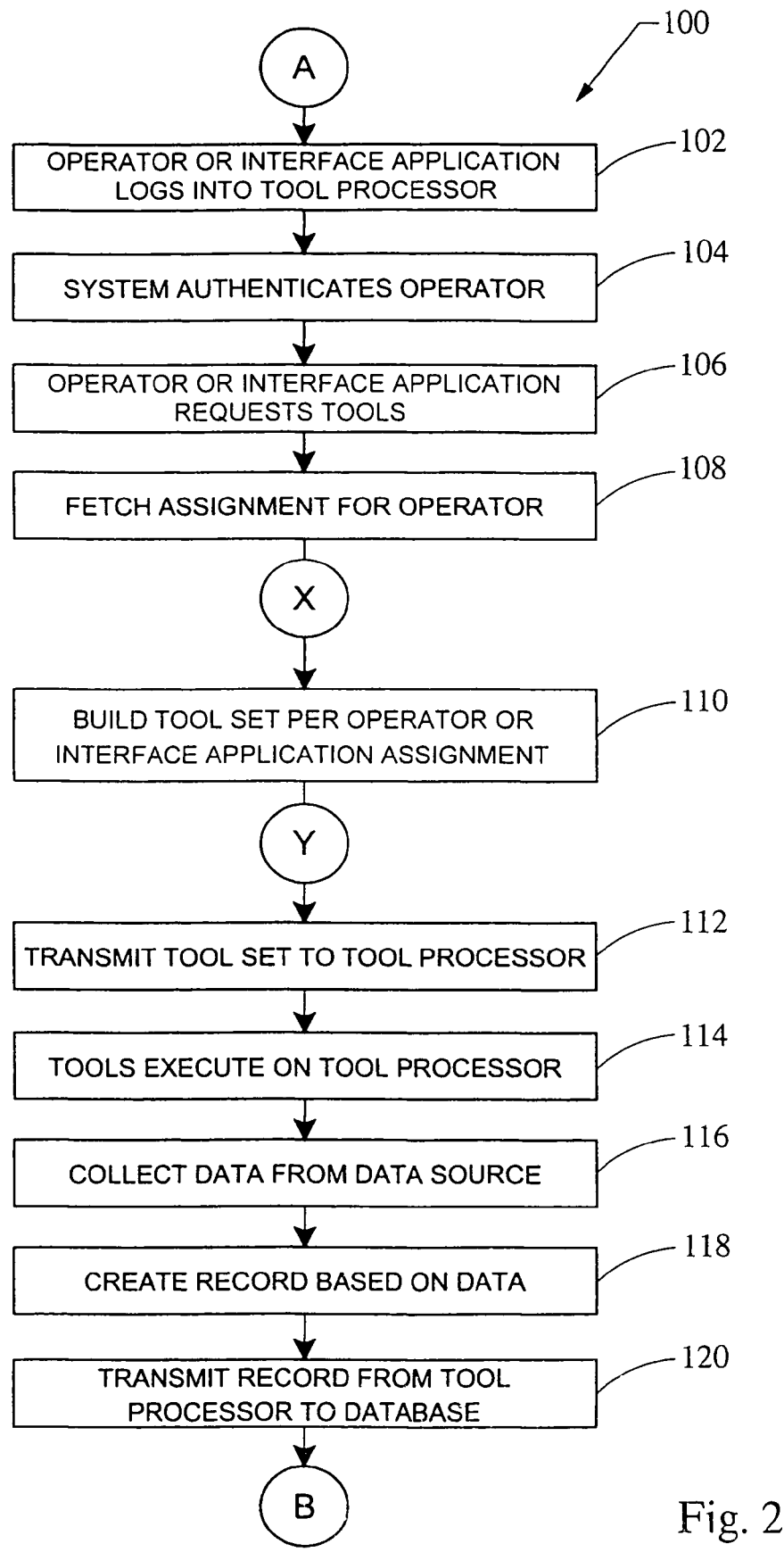
FIG. 2 is a flow chart showing the process flow of the first embodiment of the invention.

Referring now to FIG. 2, the method 100 for collecting data from a data source file 70 begins in step 102 when the operator 60 logs onto an application program containing functionality to authenticate the identity of the operator 60. The application program may reside on the tool processor 50 or on the application processor 27 of a remote server 20, or a combination of both of these configurations with some functions of the application program residing locally on the tool processor 50 and some functions of the application program residing remotely on a server 20. The application program authenticates the operator in step 104 allowing the operator in step 106 to request the appropriate tools for a particular data collection assignment. In step 108 the application program fetches the assignment for the operator 60 and begins in step 110 to build a tool set that will enable the operator 60 to collect the information or data of interest to the organization that has been authorized to receive the patient's information, such as a medical service provider plan.

In step 112, the tool set is transmitted by the tool transmitter 32 within communication system 30 from the tool collection 23 within the database 22 to the tool processor 50 via the communication channel 40. The tool set is stored in the tool store 58 within the data store 52 resident on the tool processor 50. The tools are executed by the tool parsing engine 54 within the tool processor 50 in step 114 enabling the operator 60 create data records 56 in step 118 from the relevant data collected from the source files 70. The data records 56 are stored within the data store 52 of tool processor 50. The record store 56 and the tool store 58 resident on tool processor 50 may be contained with the same or different devices.

In step 120, the data record or records 56 are transmitted from the tool processor 50 through its communication system 55 via the communication channel 40 to the data receiver 34 to a remote communication system 30 that provides a communication interface for the server 20. The data records 56 are stored in the data collection 24 residing on the server 20.

Figure 3:
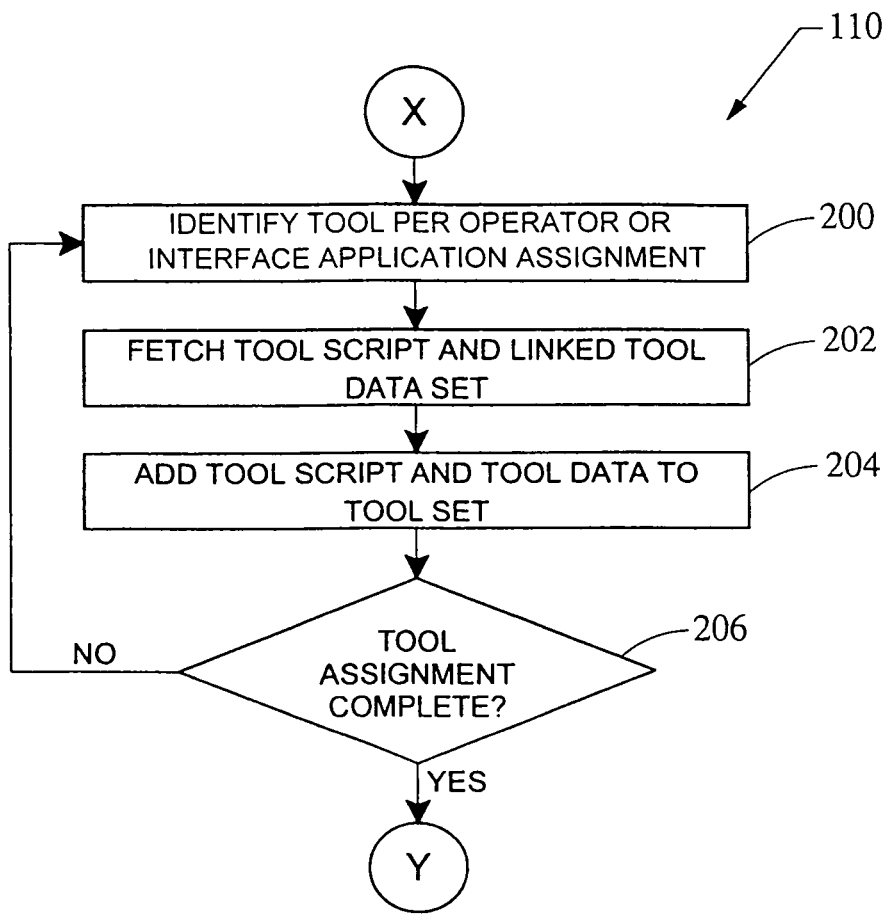
FIG. 3 is a flow chart showing the process flow for building a tool set.

The process of building the tool set for the operator's data collection assignment in step 110 is outlined in more detail in FIG. 3 beginning in step 200 in which the application program identifies a tool 25 that is needed for the operator 60 to perform his or her data collection assignment. The identity of the operator 60 may be used to determine the data collection assignment and thus serve as the basis for selecting the component tools that will comprise a tool set, although other criteria such as date, time, location and/or other relevant factors may also be used by the application program in determining the tools that will comprise the tool set to compete any particular data collection assignment. The application program fetches the tool 25 script in step 202 and the data set 26 that is linked or associated with the identified tool 25 script. In step 204 the fetched tool 25 script and data set 26 are added to a tool set for the operator's 60 assignment.

In step 206, the application program decides whether or not all of the tools 25 and linked or associated data sets 26 that are required for the operator 60 to compete the assignment have been accumulated in the tool set and returns to step 200 if all of the tools 25 and linked or associated data sets 26 have not been accumulated to complete the assignment. If all of the tools 25 and linked or associated data sets 26 required by the operator to complete the assignment have been accumulated the process continues to step 112 in which the tool set is transmitted via the communication channel 40 to the communication system 55 in the tool processor 50 as described above.

Figure 4:
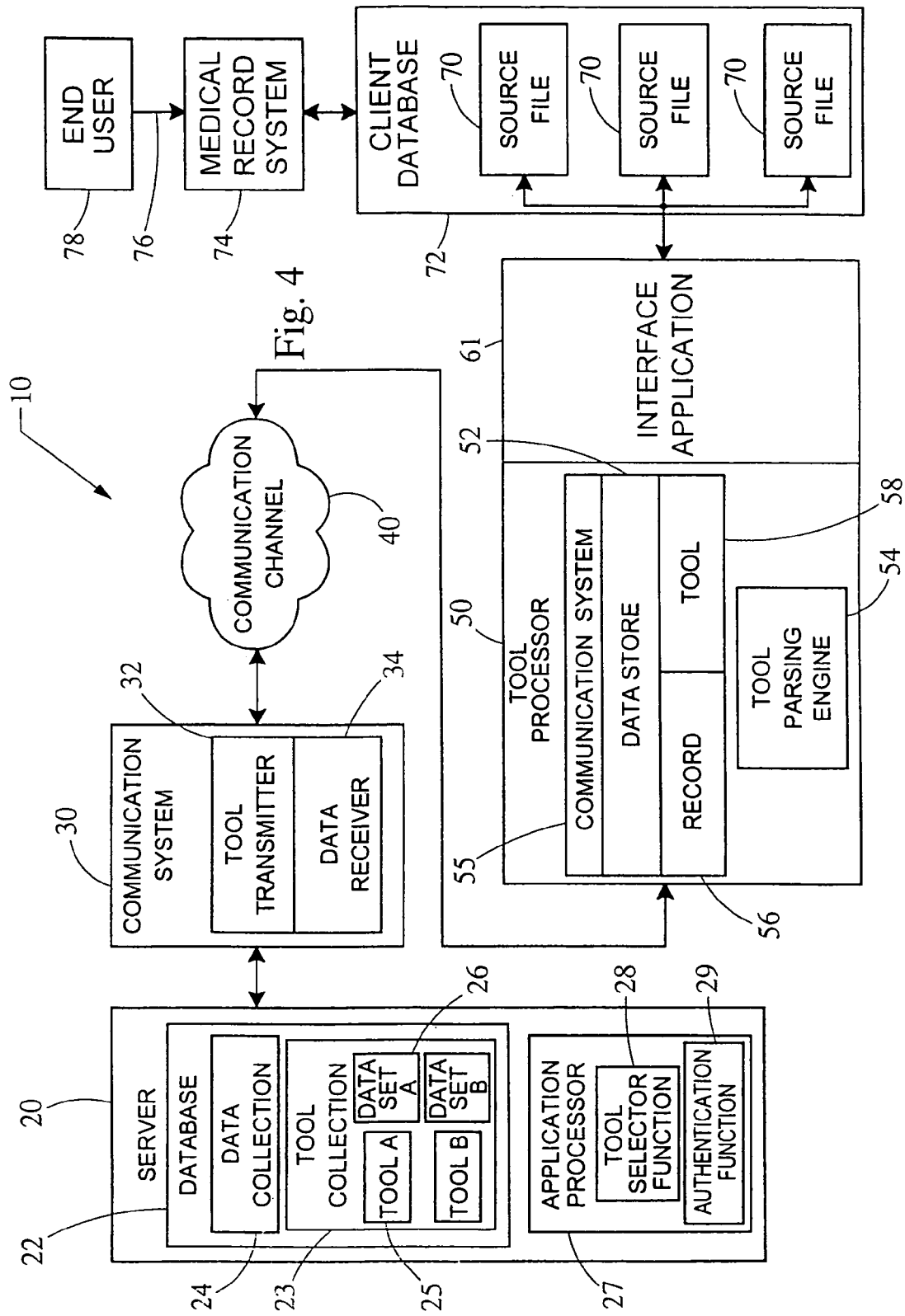
FIG. 4 is a block diagram showing the architecture and functional entities of a second embodiment of the invention in which the human operator is replaced by an interface application program.

Referring now to FIG. 4, a second preferred embodiment of the invention is depicted in which the human operator 60 has been replaced in the system 10 by an interface application program 61 running on the tool processor 50 as the interface between the tool processor 50 and the sources files 70. Like the human operator 60 in the first preferred embodiment described above, the interface application 61 searches through the source files 70 stored on a client database 72 to extract data in accordance with directions in the tool set and data set. For example, the tools set may contain instructions to collect a patient's birth date, the date of an office visit, or particular codes that indicate diagnoses or events such as doctor office or hospital visits. The interface application 61 may also be resident on the same machine as the data the tool selector function 28, the authentication function 29 and/or the database 22, or could physically reside on a separate machine that is interconnected with the system 10.

The interface application 61 can be configured such that some functions reside locally on the tool processor 50 and some functions reside remotely on a server 20. The interface application program 61 may also be part of a larger data management system that has a data collection function. The data management system can be configured to reside centrally either on the tool processor 50 or a remote server 20. The data management system can also be a distributed architecture system with some functions residing on the tool processor 50 and some functions residing remotely on a server 20. Alternatively, the interface application 61 can be configured to monitor one or more data input channels 76 between an end user 78 and an electronic medical records system 74 to extract data in real time and deliver information in smaller data packets. The interface application 61 transmits a data packet when a particular detail specified by the data set and data tools is recognized on the data input channel 76. The data tool and data set may request information related to a particular code 9999, for example, which may represent that a certain lab test has been ordered by a doctor. The interface application 61 can be configured to continuously monitor for the code 9999 and extract in real-time the fact that this test has been ordered at the same time that doctor's assistant inputs this data into the computer resident at the doctor's office. In this embodiment, the interface application 61 can be resident on a tool processor 50, a remote server 20 or on a server or workstation connected directly to a client's network with a communication channel back to the system 10.

The interface application 61 supplies the search, recognition and extraction skills that are necessary to generate the data records 56 that are supplied by the human operator 60 in the first preferred embodiment depicted in FIG. 1. The interface application 61 is a computer program that may incorporate expert systems, artificial intelligence and/or other embedded intelligence technologies for the purpose of supplying or approximating the human operator's 60 expertise, and may be written in software languages that afford learning capabilities such as 4GL. The interface application 61 may utilize any interface protocol, such as by way of example, HL7, ODBC, XML or a proprietary interface, suitable to interact with the source files 70. The interface application 61 may interact with the source files 70 through one or more computers, devices, and/or interfaces in any manner known in the art, including the Internet, intranets and through various server protocols and devices. The data may be extracted and transmitted from the device on which the source files 70 are resident and received by the interface application 61 on the remote server 20 or on the tool processor 50 in any number of ways, including, but not limited to, any data or signal discernable by the application interface 61 as a data record 56, such as a message in any format of any computer protocol.

The second preferred embodiment of the invention described above with reference to FIG. 4 for collecting data from data source files 70 utilizing the interface application 61 instead of a human operator 60 performs the method set forth in FIGS. 2 and 3 in a manner similar to collection by a human operator. The method begins in step 102 when the interface application 61 logs onto the system 100. The interface application 61 may logon to application program in response to polling that occurs at predetermined intervals established during initialization of the interface application 61.

In step 104, the application authenticates the interface application 61 based on information contained in a transmission from the interface application 61. The authentication function 29 may reside of the tool processor 50 or on a remote server 20. In step 106, the interface application 61 requests the appropriate tools for a particular data collection assignment. In step 108, the application program fetches the assignment for the application interface 61 and begins in step 110 to build a tool set in the manner set forth in FIG. 3 and described above that enables the interface application 61 to collect the information or data of interest. Once the tool set has been assembled, the tool set is sent in step 112 to the tool processor 50 and tool parsing engine 54 resident on the tool processor 50 begins in step 114 executing or parsing the script of each of the tools 25 in the tool set to collect the relevant data from the source files 70.

As the interface application 61 collects the data in step 116 from the source files 70 under the control of the tool processor 50, a data record 56 is created in step 118 and stored in the data store 52 of the tool processor 50. Once all of the instructions in the tool set have been executed and the data is completely collected in step 118 the tool processor 50 then uploads data records 56 in step 120 from the local data store 52 to the data receiver 34 and on to the data collection 24 in the database 22. Alternatively, the submission of data to the database 22 could occur in real-time as it is being collected from the source files 70 through the application interface 61. It should be noted that the functions of the interface application 61 in this process 100 could also be performed remotely by a data application program resident on a remote server 20.

Figure 5:
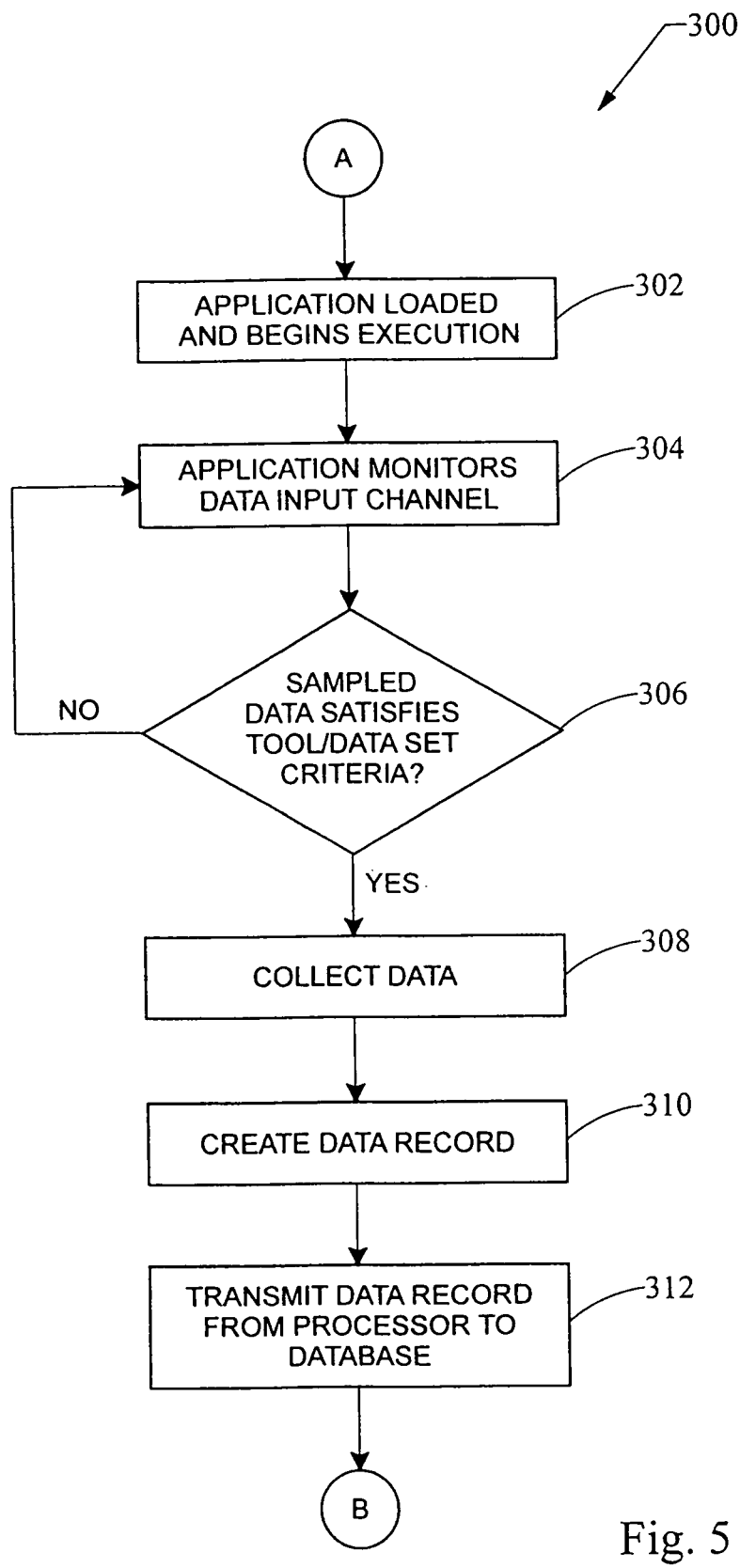
FIG. 5 is a flow chart showing the process flow of an alternative embodiment of the invention in which the human operator has been replaced by an interface application program that directly monitors a data input channel.

Referring now to FIG. 5, the second alternative method 300 for collecting data from a data source file 70 without the aid of a human operator 60 begins in step 302 as the tools and data are loaded onto the tool processor 50 and begin to execute. In step 304, the application interface monitors traffic 76 on the data input channel 76 between an end user 78 and a medical records system 74 or other type of data storage system. In step 306, the sampled data is compared to the particular criteria requested by the tool set and data set. If the sampled data does not meet the particular criteria specified by the tool set and data set, the process returns to step 304 and continues monitoring the data input line 76. If the sampled data in step 306 does meet a particular criterion specified in the tool set and data set, the data is collected in step 308. A data record is created in step 310 and the collected data transmitted to the data base 22 in step 312.

The foregoing description of the preferred embodiment is not intended to limit the invention to this preferred embodiment, but rather to enable any person skilled in the art of data collection to make and use this invention. As any person skilled in the art of data collection will recognize from the foregoing description and from the figures and claims, modifications and changes can be made to this preferred embodiment of the invention without departing from the scope of this invention defined in the following claims.

I claim:

1. An automated method for collecting data from more than one data source, each data source including a source of input data in communication with a data storage system, the method comprising the steps of:
   providing a database containing at least one data collection tool for collecting data from the more than one data source to create a record and a selector for selecting the at least one data collection tool from the database; each data collection tool being linked with a data set that contains parameters and data for execution of the data tool;
   providing a tool processor having a tool parsing engine that executes the selected at least one data collection tool;
   providing an application processor for building a tool set based on a data collection assignment relevant to medical services;
   selecting the at least one data collection tool from the database;
   building a tool set based on the data collection assignment, the tool set comprising one or more data collection tools;
   transmitting the tool set to the tool processor;
   providing an interface between the tool processor and the data sources; wherein the interface is a computer program; the interface program being configured to continuously monitor one or more data input channels located between the data sources and the data storage system for data relevant to the data collection assignment and to extract the data in real time from the one or more data input channels as the data is being transmitted to the data storage system; the data storage system being a medical records system;
   wherein the interface samples the data from the data source and compares said sample data against criteria established for the data collection assignment; the interface allowing collection of the data when the sample data matches the criteria for the data collection assignment;

wherein real time means at the same time the data is provided over the one or more data input channels from the data source to the data storage system;

collecting data relevant to the data collection assignment from the more than one data source using the tool set;

creating a data record based on the data; and transmitting the data record to the database.

2. The method of claim 1, wherein said collecting step is performed by a computer program.

3. A method for collecting data from more than one data source in real-time comprising the steps of:

providing an interface program configured to continuously monitor a communication channel located between a data storage system and more than one source of input data and to extract the data in real time from the more than one source of input data as the data is being transmitted to the data storage system; the data storage system being a medical records system;

wherein real time means at the same time the data is provided over the communication channel from the data source to the data storage system;

providing a tool processor in communication with a database and the interface program, the tool processor having a tool parsing engine that is configured to execute at least one data collection tool; each data collection tool being linked with a data set that contains parameters and data for execution of the data tool;

monitoring the communication channel for data related to medical services that match at least one predetermined criterion;

determining whether the monitored service data contains the predetermined criterion using the data collection tool; and wherein the interface program samples the data from the data source and compares said sample data against the predetermined criterion; the interface program allowing collection of the data when the sample data matches at least one predetermined criterion;

creating a data record based on at least a portion of the monitored service data that contains the predetermined criterion; and transmitting the data record to the database.

4. A computer-based system for collecting data from more than one data source, the computer-based system comprising:

at least one hardware processor that includes memory;

a database containing at least one data collection tool for collecting data from the more than one data source to create a record; each data collection tool being linked with a data set that contains parameters and data for execution of the data tool;

a tool selector for selecting the data collection tool from the database;

a tool processor having a tool parsing engine for executing the data collection tool;

a communication channel for communicating between the database and the tool processor; and an application processor for building a tool set in response to a data collection assignment; the tool set including at least one data collection tool; the application processor including an interface computer program in communication with the tool processor and the data sources by continuously monitoring the communication channel;

wherein the system collects data relevant to medical services in real time from the more than one data source according to a method comprising:

providing the database;

providing the tool selector;

providing the tool processor;

providing the application processor;

selecting the at least one data collection tool;

building the tool set;

transmitting the tool set to the tool processor;

providing the interface computer program between the tool processor and the data sources; the interface computer program being configured to continuously monitor one or more data input channels located between the data sources and the data storage system for data relevant to the data collection assignment and to extract the data in real time from the one or more data input channels as the data is being transmitted to the data storage system; the data storage system being a medical records system;

wherein the interface program samples the data from the data source and compares said sample data against criteria established for the data collection assignment; the interface program allowing collection of the data when the sample data matches the criteria for the data collection assignment;

wherein real time means at the same time the data is provided over the one or more data input channels from the data source to the data storage system;

collecting data relevant to the data collection assignment from the more than one data source using the tool set;

creating a data record based on the data; and transmitting the data record to the database.

5. The system of claim 4, wherein the system further comprises;

a remote server;

wherein the interface computer program is configured such that some of the interface computer program's functions reside locally with the tool processor and some of the interface computer program's functions resides remotely on the server.

6. The system of claim 4, wherein the interface computer program includes one selected from the group of an expert system, artificial intelligence, or another embedded intelligence technology in order to provide the search, recognition, and extraction skills necessary to create the data records.

7. The system of claim 4, wherein the interface computer program uses an interface protocol selected as one from the group of HL7, ODBC, or XML to interact with the data source.

8. The method of claim 1, wherein the method further comprises the step of authenticating the interface computer program.

* * * * *